United States Patent [19]

Rosenkoetter

[11] Patent Number: 5,590,644
[45] Date of Patent: Jan. 7, 1997

[54] HEAT AND MOISTURE EXCHANGER FOR BREATHING

[75] Inventor: Terry G. Rosenkoetter, Greenwood, Ind.

[73] Assignee: Med-Plastics, Intl., Inc., Indianapolis, Ind.

[21] Appl. No.: 545,353

[22] Filed: Oct. 19, 1995

[51] Int. Cl.$^6$ .................................................. A61M 16/00
[52] U.S. Cl. ............................. 128/201.13; 128/205.12; 128/205.27; 128/205.29; 128/204.17
[58] Field of Search ......................... 128/201.13, 205.12, 128/205.23, 205.27, 205.29, 206.16, 206.17, 207.14, 909, 911, 203.26, 203.27, 204.17, 204.18

[56] References Cited

U.S. PATENT DOCUMENTS

| | | | |
|---|---|---|---|
| 3,782,083 | 1/1974 | Rosenberg | 128/205.29 |
| 3,960,148 | 6/1976 | Dryden | 128/203.16 |
| 4,010,748 | 3/1977 | Dobritz | 128/203.27 |
| 4,787,894 | 11/1988 | Turnbyll | 128/207.14 |
| 5,035,236 | 7/1991 | Kanegaonlear | 128/205.27 |
| 5,195,527 | 3/1993 | Hicks | 128/204.17 |
| 5,337,739 | 8/1994 | Lehman | 128/205.27 |

FOREIGN PATENT DOCUMENTS

| | | | |
|---|---|---|---|
| 8904684 | 6/1989 | WIPO | 128/204.17 |

OTHER PUBLICATIONS

*3M Heat and Moisture Exchange Media*, 3M Filtration Products Advertising Sheet 70–0704–7788–3, Copyright 3M 1994.
*Performance evaluation of six heat and moisture exchangers according to the Draft International Standard (ISO/DIS 9360)*, Acta Anaesthesiol Scand 1990: 34: pp. 404–409.
*Heat and moisture exchangers with bacterial filters: a laboratory evaluation*, Acta Anaesthesiol Scand 1992: 36: pp. 572–576.
Humidification of Inspired Gases During Mechanical Ventilation, The Journal for Repiratory Care Practitioners/RT, pp. 55–66.
*Clinical Investigations in Critical Care*, Chest, vol. 104, pp. 1800–1805, Dec. 1993.
*Artificial Noses: The Unanswered Questions*, Respitory Care, Nov. '89, vol. 34, No. 11, pp. 969–971.
"The FloCare Family of Heat and Moisture Exchangers", advertising sheet, Copyright FloCare Medical, 1992.
"ThermoFlo Filter", ARC Medical, Inc., No. TFF Nov. 1992.
"Pall Heat and Moisture Exchanger Filter", Copyright 1990, 1992, Pall Corporation, Catalog AGT6937.5M.
"Temp Marq Heat and Moisture Exchangers", advertising sheet by Marquest Medical Products, Inc. 1991, Sheet No. 69110MK.
"Aqua+ Hygroscopic Condenser Humidifiers", Advertising brochure by Hudson RCI, Document No. 11–23002–70.

(List continued on next page.)

*Primary Examiner*—V. Millin
*Assistant Examiner*—V. Srivastava
*Attorney, Agent, or Firm*—Woodard, Emhardt, Naughton, Moriarty & McNett

[57] ABSTRACT

A heat and moisture exchanger (HME) media disk and associated virus and bacteria filter disk are placed in a housing of two clear plastic shells ultrasonically welded together and having ports at opposite ends of the housing for connection of flexible respiratory tubing to them. A guide vane is situated across the port at the patient end of the housing and extends into the HME and provides turbulence for efficient usage of the media for heat and moisture exchange functions. Vanes are provided in the housing adjacent the machine end port of the housing. A carbon dioxide sampling tap is provided on the machine end portion of the housing. The vanes are tapered from a small or narrow edge at the disk surface to thicker cross sections at increasing distances from the disk toward the housing end ports. Provision for connections to standard tubing is made at the ports.

15 Claims, 5 Drawing Sheets

OTHER PUBLICATIONS

"BB25A Pall Small Vol. Heat and Moisture Exchanger Filter With $CO_2$ Monitoring Port", Advertising sheet by Pall Corporation 1992, AGT49220M.

"HME15–22M Pall Heat and Moisture Exchanger Filter With $CO_2$ Monitoring Port", advertising sheet by Pall Corporation 1993, QCP49315M.

"Pulmonary Management Systems for Humid–Vent Humidification Management Systems" brochure by Gibeck–Dryden.

5,590,644

HEAT AND MOISTURE EXCHANGER FOR BREATHING

BACKGROUND OF THE INVENTION

1. Field of the Invention:

This invention relates generally to breathing systems and more particularly to an improved heat and moisture exchanger device for such systems.

2. Description of the Prior Art:

Many healthcare services employ breathing systems for patients. A couple of examples are anesthesia and respiratory therapy. Such procedures often involve the use of heat and moisture exchange devices which collect heat and moisture from gases exhaled from the patient, and return heat and moisture to inhaled gases, thereby minimizing or avoiding the need for external heating and humidification of inhaled gases. Devices for such purposes are well known but, in many instances, seem to be comparatively expensive and inefficient. My invention is intended to overcome such shortcomings of prior art products.

SUMMARY OF THE INVENTION

Described briefly according to a typical embodiment of the present invention, a heat and moisture exchanger includes a housing having a central axis and ports at opposite ends of the housing for connection of flexible respiratory tubing to them. One of the ports is for the tubing at the patient end of the respiratory system, so this end of the housing will be referred to as the patient end. The other of the ports is for connection of the tubing to a respirator or gas machine, so this end of the housing will be referred to as the machine end. A heat and moisture exchange (HME) media disk, and a filter disk are contained in the housing across the path between the patient end port and the machine end port. A guide and distribution vane is provided across the patient end port, and has its inner edge against the patient end facing surface of the HME media and provides turbulence facilitating distribution of exhaled gases throughout the exposed surface of the media. The vane has a decreasing cross-sectional thickness at increasing distances from the patient end toward the machine end, with the thin end of the vane snugly engaging the HME media. The filter disk for bacteria and virus control is located at the machine end face of the media, and extends entirely across the flow path through the housing. It is held in place by two vanes of wedge-shaped cross section and which extend inside the housing, axially and radially outward from the machine end port, to the filter. A gas sampling connector tap is provided on the machine end portion of the housing. The machine end vanes are also tapered from a small or narrow edge at the filter surface to thicker cross sections at increasing distances from the filter toward the machine end of the housing.

DESCRIPTION OF THE PREFERRED EMBODIMENT

Figure 1:
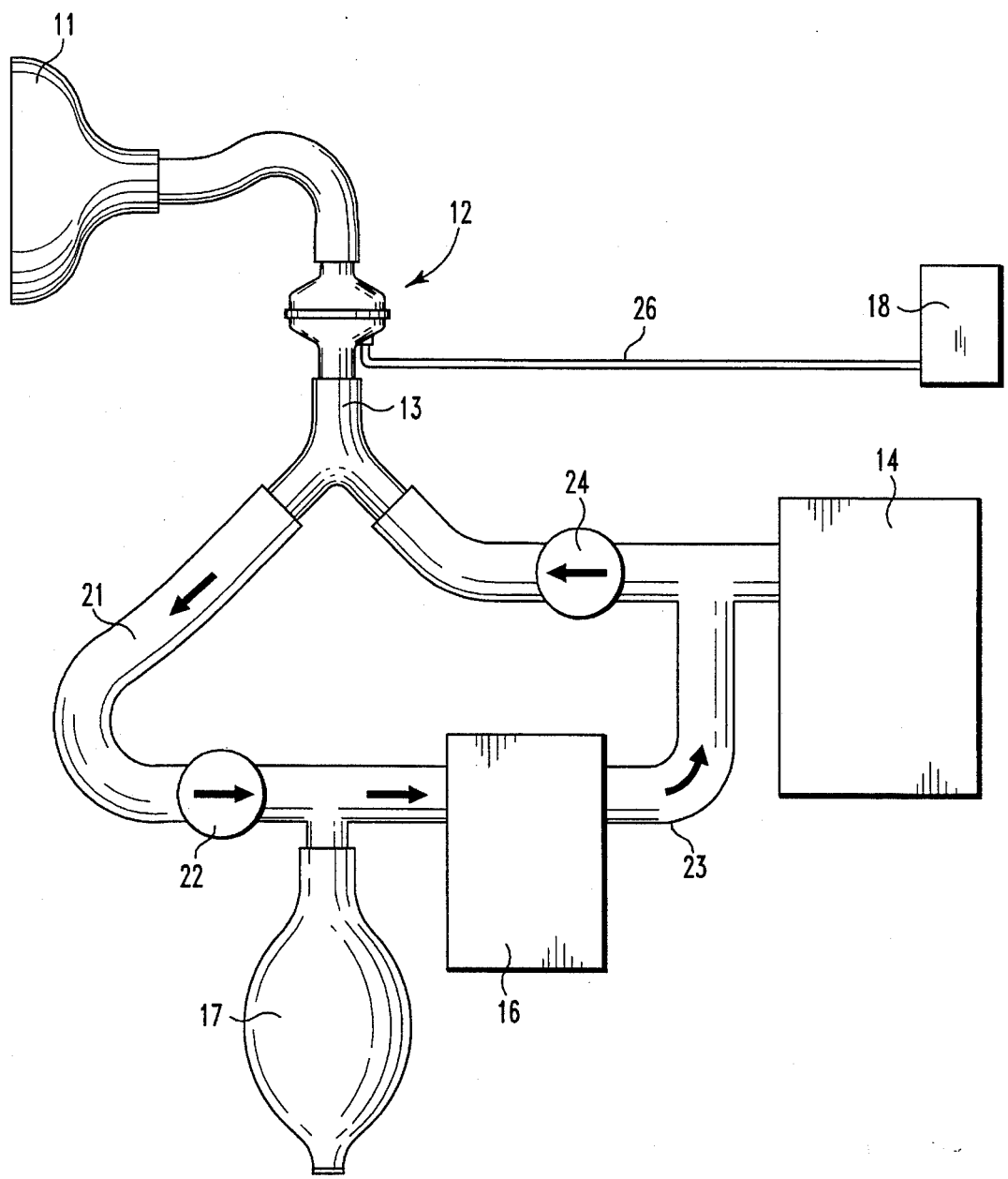
FIG. 1 is a schematic diagram of a rebreathing circuit with the heat and moisture exchanger device of the present invention incorporated therein.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, and particularly FIG. 1, there is shown a typical multi-limb circle absorption anesthesia circuit. It includes a patient mask 11, the heat and moisture exchanger device 12 of the present invention, a wye fitting 13, a breathing gas supply machine 14, a carbon dioxide absorber 16, a flexible gas reservoir 17 (rebreathing bag), and a carbon dioxide analyzer 18. Gas exhaled by the patient passes from the wye fitting 13 through the return line 21 and the one-way valve 22 and the carbon dioxide absorber 16 and back through recirculation line 23 and one-way valve 24 to the wye fitting for inhalation by the patient. To the extent anesthetic gas or fresh oxygen are required, they can be added from the gas machine 14. Excess pressure venting can be provided at any suitable location and, if desired, coupled to an external vent to avoid undesired communication with the room atmosphere. A gas sampling line 26 is connected to the carbon dioxide analyzer 18 and takes gas from a location near the patient to monitor the carbon dioxide level in the exhaled air.

Figure 2:
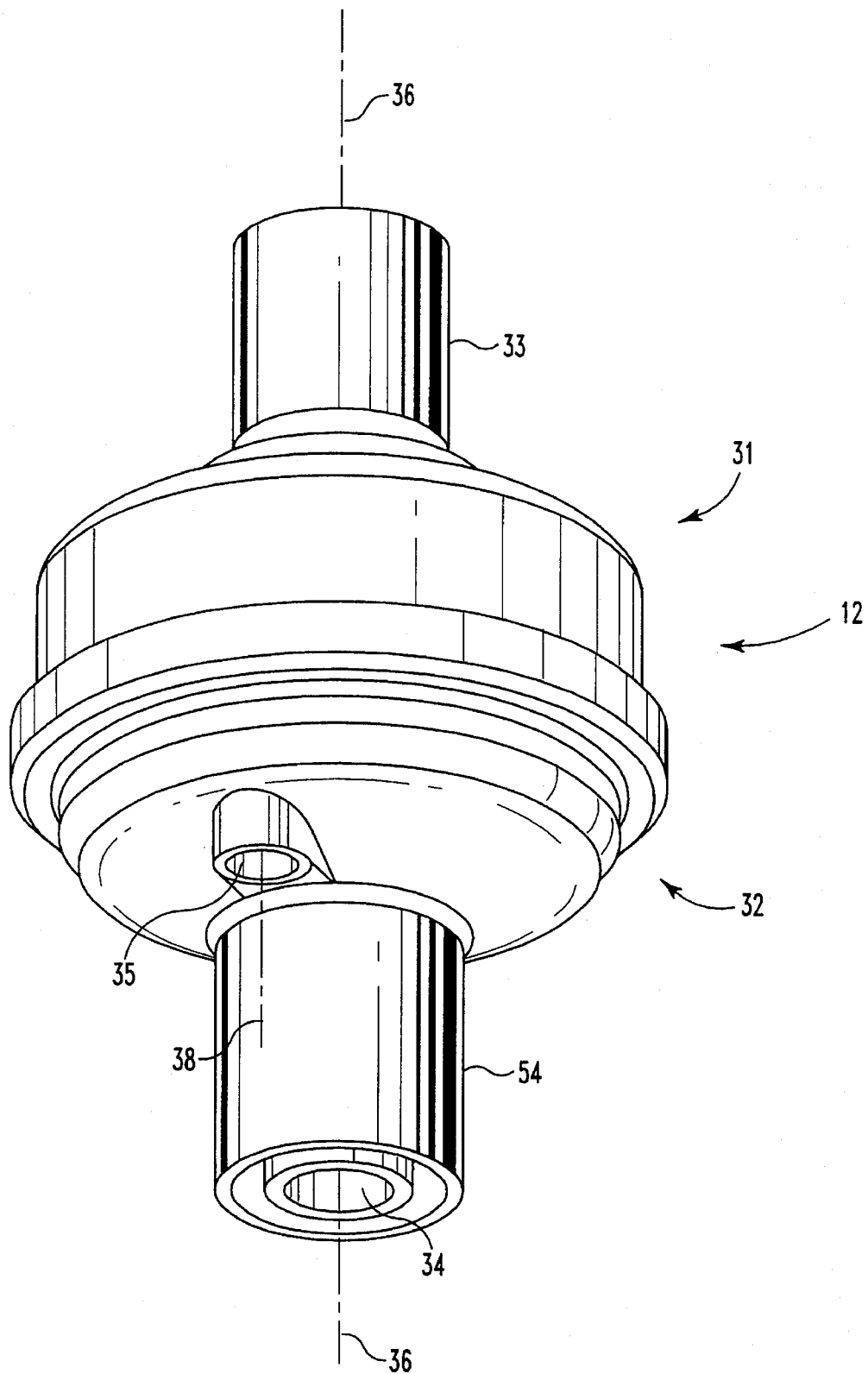
FIG. 2 is a pictorial view of the device.

Referring now to FIG. 2, which is a pictorial view of the heat and moisture exchanger device, there are top and bottom generally bell-shaped shells 31 and 32 of clear plastic with integral tubular stubs defining ports 33 and 34 thereon, all aligned on the axis 36. A gas sampling port 35 is adjacent port 34 and also has an axis 38 parallel to axis 36.

Figure 3:
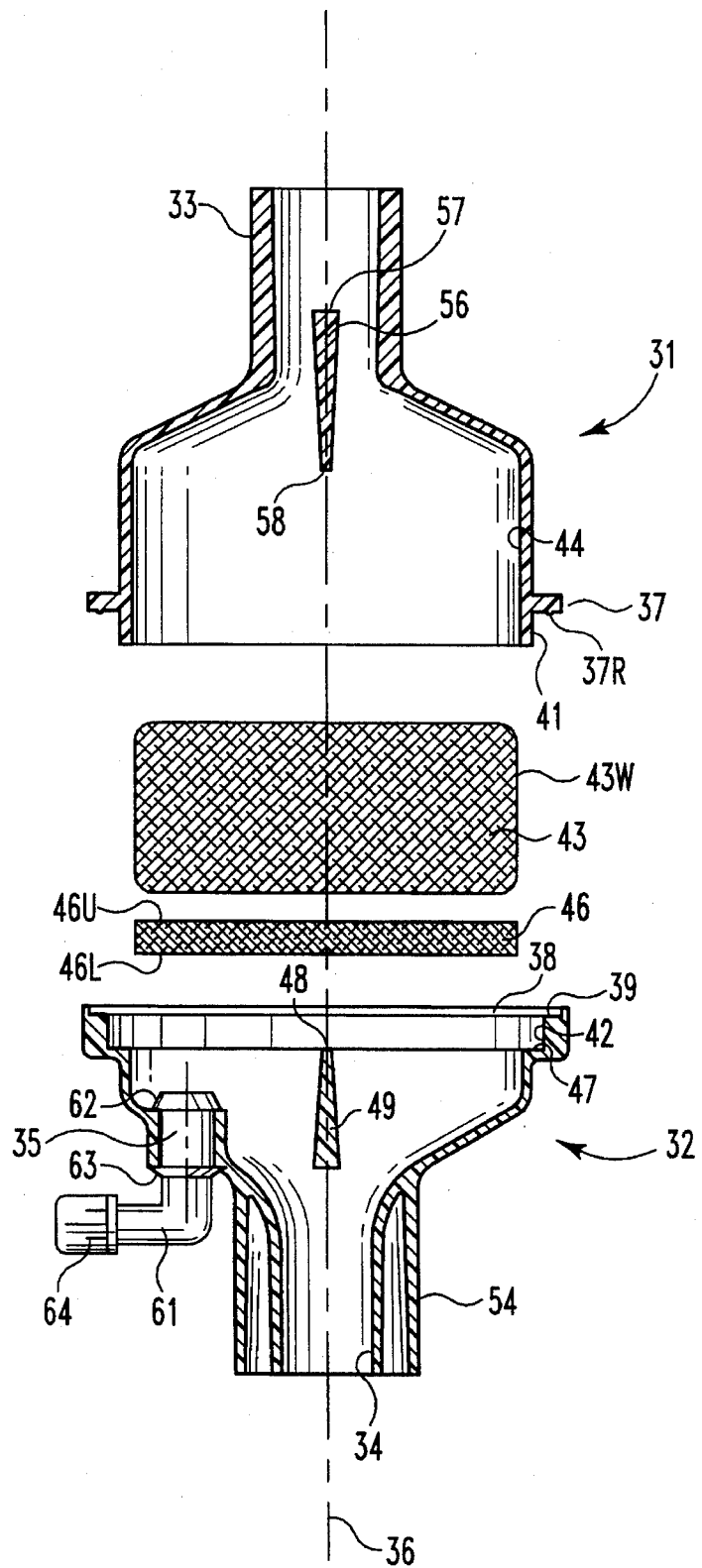
FIG. 3 is an exploded longitudinal sectional view thereof.
Figure 4:
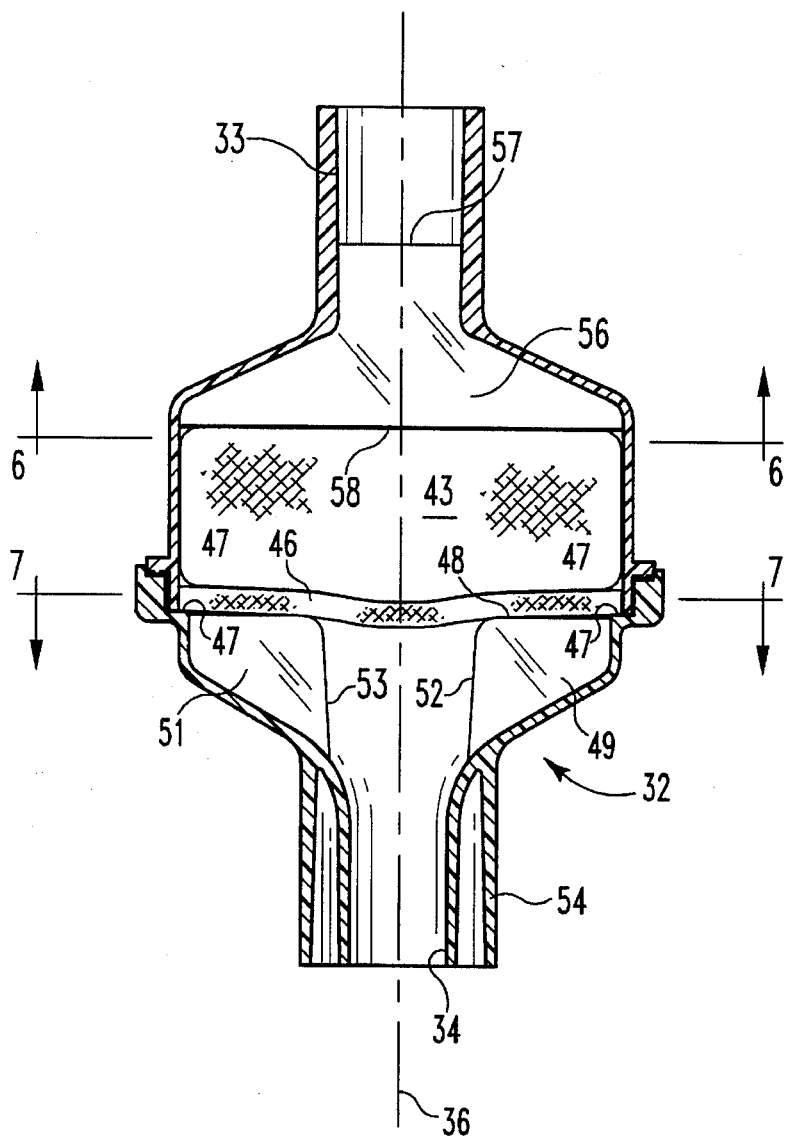
FIG. 4 is a longitudinal sectional view of the assembly.
Figure 5:
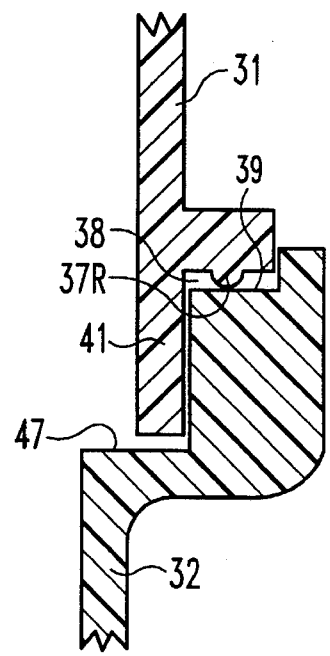
FIG. 5 is an enlarged fragmentary portion of the joint between the two shells of the housing.
Figure 6:
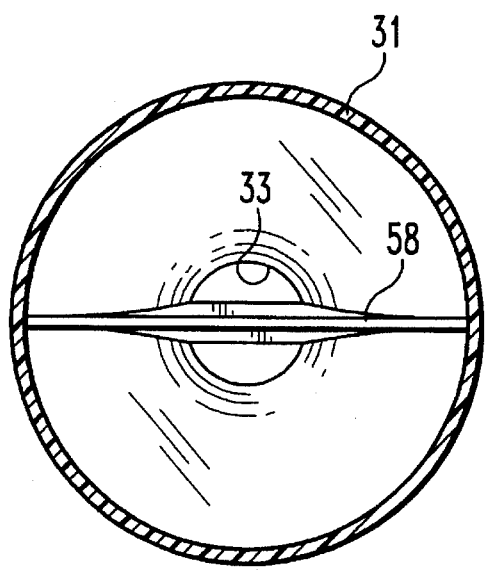
FIG. 6 is a cross section taken at line 6—6 in FIG. 4 and viewed in the direction of the arrows.
Figure 7:
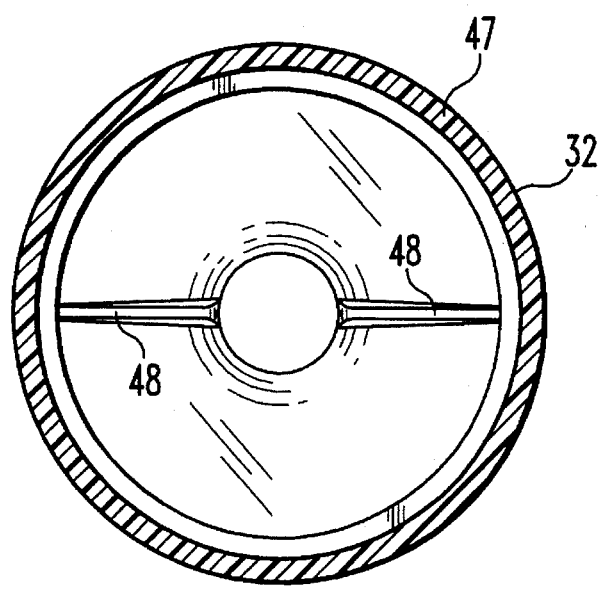
FIG. 7 is a cross section taken at line 7—7 in FIG. 4 and viewed in the direction of the arrows.

As best shown by comparison of FIGS. 3 and 4, shell 31 has an outwardly extending perimetrical flange 37 which is received in recess 38 of the shell 32 where it rests on shoulder 39. There is a ridge 37R on the underside of flange 37. The sub-flange wall 41 of shell 31 is fittingly received in the bore 42 of the shell 32, above shoulder 47. A hydroscopic media disk 43 is fittingly received in the cylindrical inner wall 44 of shell 31. A hydrophobic filter disk 46, for exclusion of bacteria and viruses is located under disk 43. The outer edges of the filter disk 46 seal on the shoulder 47 of shell 32. After installation of the disks, the shells are secured together by ultrasonic welding of the flange 37 to the shoulder 39. Thus, the disks extend entirely across the flow path of gases through the housing assembly from the one port to the other, and divide the housing into two chambers, the patient end chamber and the machine end chamber.

The lower face 46L of the filter disk 46 is not only supported on the shoulder 47, but also on the upper edges 48 of two vanes 49 and 51 which, as shown in FIG. 4, extend inwardly from shoulder 47 toward axis 36 but terminate at edges such as 52 and 53 which extend generally parallel to the axis 36 and are slightly outboard of an upward projection of the cylinder of the machine end port 34 at the lower end of shell 32. As best shown in FIG. 3 for vane 49, these vanes 49 and 51 taper outwardly from a narrow upper edge 48 at the filter disk and increase in cross-sectional thickness as they extend downward toward the machine end port.

A vane 56 extends diametrically across the upper shell end fitting 33 on the center line 36. It has a flat upper edge 57 and a narrow lower edge 58 which, in the assembly as shown in FIG. 4, is slightly embedded in the center of the disk 43 all the way across the diameter of the housing. In the assembly, this vane securely locates the disk 43 between that edge 58 and the abuttingly engaging upper face 46U of the filter disk 46 and forces the combination of the disk 43 and filter disk 46 down snug against the shoulder 47 and vanes 49 and 51, and also assures that the peripheral wall 43W of the disk 43 will snugly engage the cylindrical wall 44 around the entire circumference of the shell 31.

An elbow 61 having a flange 62 at the upper end and flange 63 spaced below it is pushed up into the port 35 providing a snap-in swivel connection for a gas sampling line such as 26 in FIG. 1. The outlet end of the elbow is shown capped with a cap 64 in FIG. 3.

For purposes of example only, nominal dimensions can be given as follows:

Diameter at port 33: 22 mm outside; 15 mm inside

Upper edge thickness at 57 of vane 56: 3 mm

Lower edge thickness at 58 of vane 56: 1 mm

Distance of upper edge of vane 56 from upper edge of port 33: 15 mm

Height of vane from edge 57 to edge 58: 22 mm

Thickness of media 43 and filter 46 from edge 58 to shoulder 47: 20 mm

Diameter at port 34:
    inner cylinder, 11 mm inside; 15 mm outside;
    outer cylinder 54, 22 mm inside; 24 mm outside Horizontal distance between edges 52 and 53 of vanes 49 and 51: 18 mm Thickness of upper edge 48 of vane 49: 1 mm Diameter of wall 44: 60 mm Brand of media 43: 3M HME H-845 Media Brand of filter 46: 3M G-200

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A heat and moisture exchanger device for a breathing system and comprising:
    a housing having a patient end port and a machine end port and a passageway in the housing providing communication between the ports through the housing passageway;
    heat and moisture exchange media in the housing and extending entirely across the passageway defining a patient end chamber associated with the patient end port, and a machine end chamber associated with the machine end port; and
    a first vane dividing the patient end chamber, and having a flat edge facing away from the media and bisecting the patient end port.

2. The device of claim 1 and wherein the edge is in the patient end port and occupies between 20 and 30 percent of the patient end port area.

3. The device of claim 1 and further comprising: a filter extending entirely across the machine end chamber.

4. The device of claim 3 and wherein: the filter is a hydrophobic virus and bacteria filter which abuts the media.

5. A heat and moisture exchanger device a breathing system and comprising:
    a housing which is circular about an axis and having a patient end port and a machine end port and a passageway in the housing providing communication between the ports through the housing passageway;
    heat and moisture exchange media in the housing and extending entirely across the passageway defining a patient end chamber associated with the patient end port, and a machine end chamber associated with the machine end port;
    a first vane dividing the patient end chamber; and
    second and third vanes located in the machine end chamber and extending radially outward from a circle centered on the axis, to the inner periphery of the machine end chamber.

6. The device of claim 5 and wherein: the housing is circular about an axis; the ports are centered on the axis; the first vane extends diametrically across the first chamber and into the first port.

7. The device of claim 6 and wherein:
    the first vane is wedge-shaped in axially extending cross section, with the thick edge of the wedge in the first port, and the thin edge in the media.

8. The device of claim 6 and wherein:
    the axis lies in the first vane.

9. The device of claim 5 and wherein:
    the second and third vanes are wedge-shaped in axially extending longitudinal section.

10. The device of claim 5 and wherein:
    a filter extends across the machine end chamber;
    the second and third vanes have thin edges engaging a machine end port facing surface of the filter and confining it in place between the chambers.

11. A heat and moisture exchanger device for a breathing system and comprising:
    a housing a having patient end port and a machine end port and a passageway in the housing providing communication between the ports through the housing passageway;
    heat and moisture exchange media in the housing and extending entirely across the passageway defining a patient end chamber associated with the patient end port, and a machine end chamber associated with the machine end port;
    a first vane dividing the patient end chamber; and
    second and third vanes in the machine end chamber;
    the housing being symmetrical about an axis;
    the vanes being wedge-shaped;
    the first vane lying in a first plane containing the axis; and
    the second and third vanes lying in a second plane containing the axis.

12. The device of claim 11 and wherein:
    the machine end port is defined by a tubular stub and is surrounded by a coaxial spaced second tubular stub for connection of airway tubing thereto.

13. The device of claim 12 and wherein:
    the first mentioned tubular stub has a 15 mm OD and the second mentioned tubular stub has a 22 mm ID.

14. The device of claim 13 and further comprising:
    a gas sampling port with a snap-in swivel elbow on the machine end chamber.

15. The device of claim 11 and wherein: the media is 3M HME H-845.

* * * * *